(12) United States Patent
Vasan et al.

(10) Patent No.: US 10,578,543 B2
(45) Date of Patent: Mar. 3, 2020

(54) RANKING PIPES FOR MAINTENANCE IN PIPE NETWORKS USING APPROXIMATE HYDRAULIC METRICS

(71) Applicant: TATA CONSULTANCY SERVICES LIMITED, Mumbai (IN)

(72) Inventors: Arunchandar Vasan, Chennai (IN); Gollakota Phani Bhargava Kaushik, Chennai (IN); Abinaya Manimaran, Chennai (IN); Venkatesh Sarangan, Chennai (IN); Anand Sivasubramaniam, Chennai (IN)

(73) Assignee: Tata Consultancy Services Limited, Mumbai (IN)

( * ) Notice: Subject to any disclaimer, the term of this patent is extended or adjusted under 35 U.S.C. 154(b) by 434 days.

(21) Appl. No.: 15/473,433

(22) Filed: Mar. 29, 2017

(65) Prior Publication Data

US 2018/0149580 A1 May 31, 2018

(30) Foreign Application Priority Data

Nov. 25, 2016 (IN) .............................. 201621040374

(51) Int. Cl.
*G06F 17/50* (2006.01)
*G01N 19/08* (2006.01)
(Continued)

(52) U.S. Cl.
CPC ............. *G01N 19/08* (2013.01); *E03B 7/003* (2013.01); *E03B 7/02* (2013.01); *E03B 7/075* (2013.01);
(Continued)

(58) Field of Classification Search
None
See application file for complete search history.

(56) References Cited

U.S. PATENT DOCUMENTS 4,712,182 A * 12/1987 Wakamori .......... G01M 3/2807
702/36
5,708,195 A * 1/1998 Kurisu ...................... F17D 5/02
340/605
(Continued)

FOREIGN PATENT DOCUMENTS

CN 103258243 A 8/2013

OTHER PUBLICATIONS

Name of the author: Posted by: data61 Title of the article: Water pipe failure prediction Date: Apr. 29, 2015 Page(s) Volume-issue number(s): Publisher: : Data61, CISRO.
(Continued)

*Primary Examiner* — Kibrom K Gebresilassie
(74) *Attorney, Agent, or Firm* — Finnegan, Henderson, Farabow, Garrett & Dunner LLP

(57) ABSTRACT

Conventional systems for monitoring pipe networks are generally not scalable, impractical in the field with uncontrolled environments or rely of static features of pipes that are vary depending on the pipes under consideration. The ideal sensor-ed monitoring systems are not economically viable. Systems and methods of the present disclosure provide an improved data-driven model to rank pipes in the order of burst probabilities, by including dynamic feature values of pipes such as pressure and flow that depends on network structure and operations. The present disclosure enables estimating approximate values for the dynamic features since they are hard to estimate accurately in the absence of a calibrated hydraulic model. The present disclosure also validates the estimated approximate dynamic feature values for the purpose of estimating bursts likelihood vis-a-vis accurate values of the dynamic metrics.

13 Claims, 13 Drawing Sheets

(51) Int. Cl.
*E03B 7/00* (2006.01)
*F17D 5/02* (2006.01)
*E03B 7/07* (2006.01)
*E03B 7/02* (2006.01)
*G01N 7/00* (2006.01)
*G01V 99/00* (2009.01)
*G06Q 50/06* (2012.01)
*G06G 7/50* (2006.01)
*F17D 1/00* (2006.01)

(52) U.S. Cl.
CPC ............... *F17D 5/02* (2013.01); *G01N 7/00* (2013.01); *G01V 99/005* (2013.01); *G06F 17/5009* (2013.01); *F17D 1/00* (2013.01); *G06F 2217/34* (2013.01); *G06G 7/50* (2013.01); *G06Q 50/06* (2013.01)

(56) References Cited

U.S. PATENT DOCUMENTS

| | | | | |
|---|---|---|---|---|
| 6,247,455 | B1* | 6/2001 | Otake | F02B 75/243 123/435 |
| 7,039,565 | B1* | 5/2006 | Jin | G06F 17/5004 703/2 |
| 7,437,267 | B2* | 10/2008 | Oka | G06Q 10/06 702/181 |
| 8,510,080 | B2* | 8/2013 | Hauffen | G06F 17/00 702/181 |
| 2003/0182354 | A1* | 9/2003 | Scheidt | G06F 8/24 718/106 |
| 2004/0148113 | A1* | 7/2004 | Sage | F17D 5/02 702/51 |
| 2005/0246112 | A1* | 11/2005 | Abhulimen | F17D 5/02 702/51 |
| 2012/0013483 | A1* | 1/2012 | Jung | H04Q 9/00 340/870.16 |
| 2012/0185184 | A1 | 7/2012 | Armon et al. | |
| 2013/0211797 | A1* | 8/2013 | Scolnicov | G06Q 10/0639 703/2 |
| 2013/0332397 | A1* | 12/2013 | Scolnicov | G06Q 50/06 705/400 |
| 2014/0330749 | A1* | 11/2014 | Candas | G06Q 40/06 705/36 R |

OTHER PUBLICATIONS

Title of the article: Advanced Condition Assessment & Pipe Failure Prediction Title of the item : Fact Sheet Date: Aug. 2014 pp. 3 pages Publisher: Critical Pipes 2015 © —by Inspire Design.

Name of the author: Posted by: data61, Contact: Fang Chen Title of the article: Critical Water Main Failure Prediction Date: Feb. 24, 2015 Publisher: Data61, CISRO.

Name of the author: Jaime Valls Miro*, Jeya Rajalingam**, Teresa Vidal-Calleja*, Freek de Bruijn*, Roger Wood, Dammika Vitanage, Nalika Ulapane*, Buddhi Wijerathna* and Daoblige Su* Title of the article: A Live Test-Bed for the Advancement of Condition Assessment and Failure Prediction Research on Critical Pipes Title of the item : Date: Jun. 2014 Volume-issue number(s): Issue 2 vol. 10 Publisher: © IWA Publishing 2014.

Name of the author: Orazio Giustolisi, Dragan A. Savic, Daniele Laucelli Title of the article: Data Mining for Management and Rehabilitation of Water Systems: The Evolutionary Polynomial Regression Approac Title of the item : Water engineering communications, Institute of Hydraulic Engineering and THM at TU Dresden Date: 2004 pp. 295-296 Institute of Hydraulic Engineering and THM at TU Dresden.

Name of the author: Ami Preis1, Andrew Whittle 2 and Avi Ostfeld 3 Title of the article: On-line hydraulic state prediction for water distribution systems Title of the item : Conference Information , World Environmental and Water Resources Congress 2009 May 17-21, 2009 | Kansas City, Missouri, United States Date: Apr. 26, 2012 pp. 1-23 Publisher: © 2009 American Society of Civil Engineers.

* cited by examiner

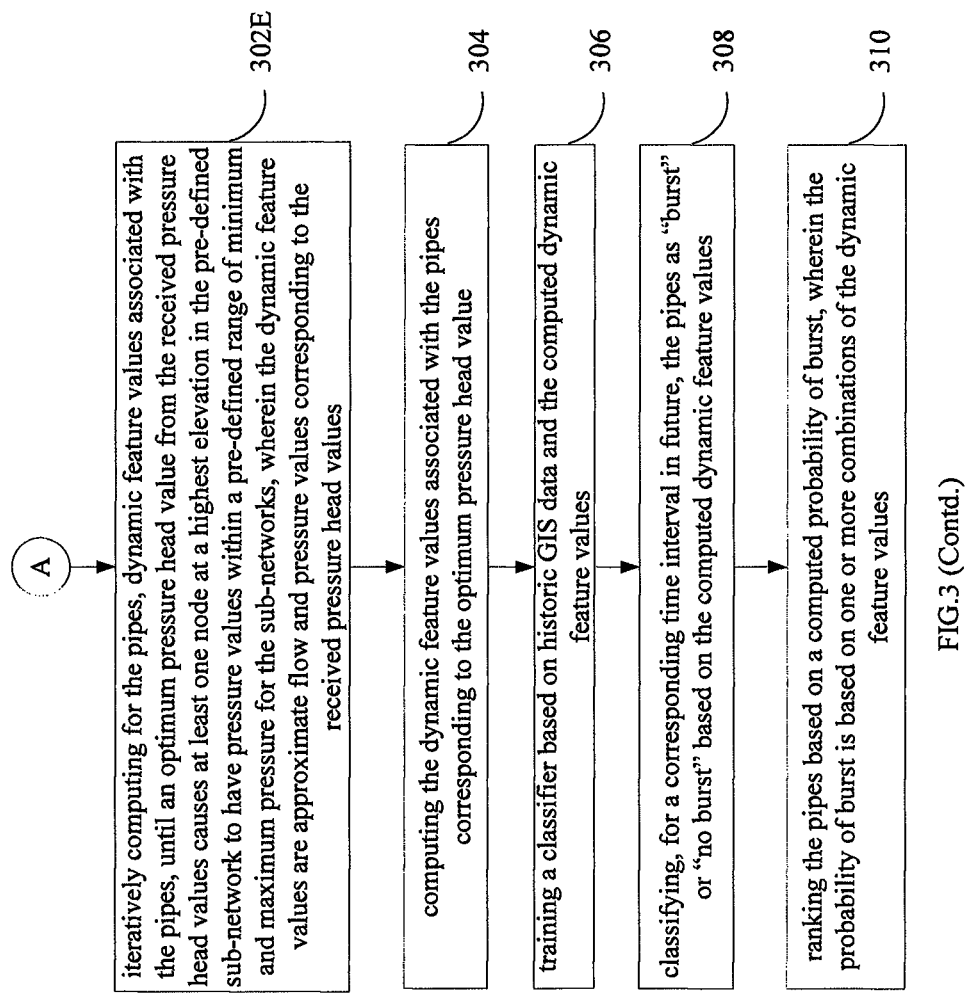
FIG.3 (Contd.)

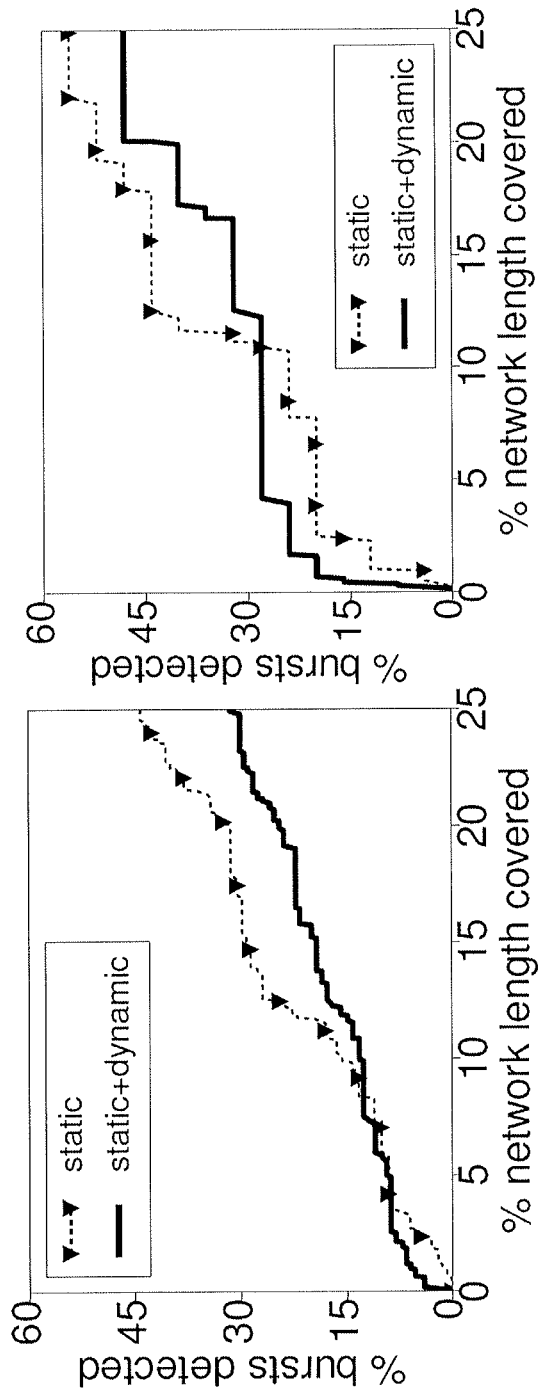

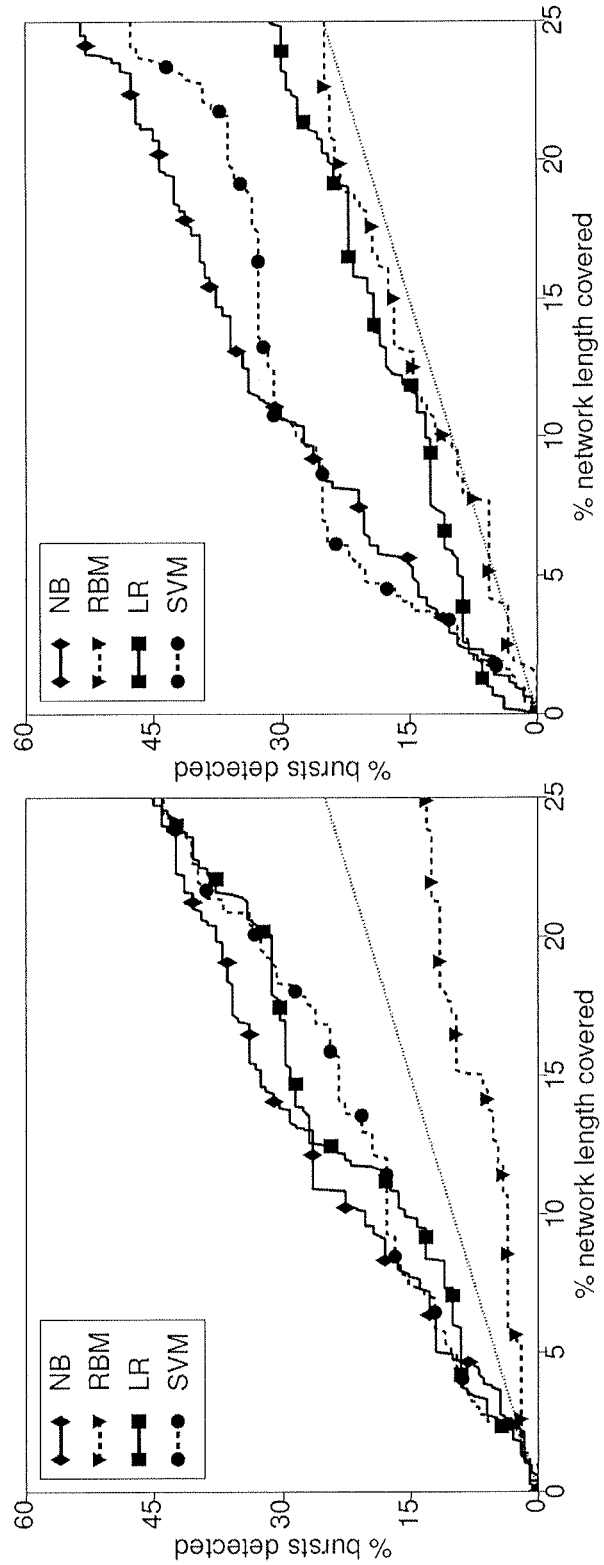

… (1) …

RANKING PIPES FOR MAINTENANCE IN PIPE NETWORKS USING APPROXIMATE HYDRAULIC METRICS

PRIORITY CLAIM

This U.S. patent application claims priority under 35 U.S.C. § 119 to: Indian Application No. 201621040374 filed on Nov. 2, 2016. The entire contents of the aforementioned application are incorporated herein by reference.

TECHNICAL FIELD

The embodiments herein generally relate to maintenance of pipes in pipe networks, and more particularly to systems and methods for ranking pipes for maintenance using approximate hydraulic metrics.

BACKGROUND

Utilities such as water, oil and gas prefer proactive rehabilitation of pipes annually to avoid bursts. The goal is to optimize use of maintenance budget by identifying pipes which are most likely to burst over the next year and fix them to reduce pipe bursts. Because pipe bursts are stochastic, it is important to predict the pipes that are most likely to burst over the next year and fix them in order to reduce the likelihood of pipe bursts.

Utilities typically have a deterministic set of rules that evaluate the risk associated with each pipe and evaluate a risk-reward matrix with the risk (probability of failure) characterized by simple approaches like the inverse of the average life-time of the pipe; and the reward characterized by the damages avoided due to the proactive pipe repair. Low-level physically-based approaches include modeling the pipe degradation by material properties. However, these approaches towards better modeling of individual pipes are not typically scalable and somewhat impractical in the field with uncontrolled environments. Higher-level data-driven approaches model the pipes by learning the probability of failures from past history of bursts. The typical features include static pipe-level metrics such as length, diameter, age, etc., that are independent of other pipes. Existing works tend to ignore dynamic features because the features need to be measured or are difficult to obtain accurately using a well-calibrated hydraulic model. Utilities such as water utilities that do not have generous budgets to do proactive pipe monitoring and maintenance find it very challenging to maintain large pipe networks. Placing a network of sensors for detecting and reacting to bursts in real-time is an ideal solution, however they are expensive to deploy and maintain at scale.

SUMMARY

Embodiments of the present disclosure present technological improvements as solutions to one or more of the above-mentioned technical problems recognized by the inventors in conventional systems.

In an aspect, there is provided a processor implemented method comprising: approximating realizable flow and pressure values for each pipe in a pipe network characterized by pre-defined sub-networks. In an embodiment, the step of approximating comprises: receiving geographic information system (GIS) data pertaining to the pipe network, the GIS data including static feature values associated with pipes in the pipe network, the static features comprising one or more of diameter, length, age, connectivity, depth, past bursts data and material associated with the pipes; generating a graph for each of the pre-defined sub-networks, wherein each pipe in the pipe network is represented as an edge and end points of each pipe in the pipe network is represented as a node in the graph; simulating a reservoir in place of an inlet pipe to each of the pre-defined sub-networks; receiving an array of permissible pressure head values for the simulated reservoir; and iteratively computing for the pipes, dynamic feature values associated with the pipes, until an optimum pressure head value from the received pressure head values causes at least one node at a highest elevation in the pre-defined sub-network to have pressure values within a pre-defined range of minimum and maximum pressure for the sub-networks, wherein the dynamic feature values are approximate flow and pressure values corresponding to the received pressure head values. The processor implemented method further comprises computing the dynamic feature values including flow, mid-point static pressure, mid-point total pressure, static pressure difference and total pressure difference associated with the pipes corresponding to the optimum pressure head value.

In another aspect, there is provided a system comprising: one or more data storage devices operatively coupled to the one or more processors and configured to store instructions configured for execution by the one or more processors to: approximate realizable flow and pressure values for each pipe in a pipe network characterized by pre-defined sub-networks, the step of approximating comprising: receiving geographic information system (GIS) data pertaining to the pipe network, the GIS data including static feature values associated with pipes in the pipe network, the static features comprising one or more of diameter, length, age, connectivity, depth, past bursts data and material associated with the pipes; generating a graph for each of the pre-defined sub-networks, wherein each pipe in the pipe network is represented as an edge and end points of each pipe in the pipe network is represented as a node in the graph; simulating a reservoir in place of an inlet pipe to each of the pre-defined sub-networks; receiving an array of permissible pressure head values for the simulated reservoir; and iteratively computing for the pipes, dynamic feature values associated with the pipes, until an optimum pressure head value from the received pressure head values causes at least one node at a highest elevation in the pre-defined sub-network to have pressure values within a pre-defined range of minimum and maximum pressure for the sub-networks, wherein the dynamic feature values are approximate flow and pressure values corresponding to the received pressure head values. The one or more processors are further configured to compute the dynamic feature values including flow, mid-point static pressure, mid-point total pressure, static pressure difference and total pressure difference associated with the pipes corresponding to the optimum pressure head value.

In yet another aspect, there is provided a computer program product comprising a non-transitory computer readable medium having a computer readable program embodied therein, wherein the computer readable program, when executed on a computing device, causes the computing device to: approximate realizable flow and pressure values for each pipe in a pipe network characterized by pre-defined sub-networks, the step of approximating comprising: receiving geographic information system (GIS) data pertaining to the pipe network, the GIS data including static feature values associated with pipes in the pipe network, the static features comprising one or more of diameter, length, age, connectivity, depth, past bursts data and material associated with the pipes; generating a graph for each of the pre-defined sub-networks, wherein each pipe in the pipe network is represented as an edge and end points of each pipe in the pipe network is represented as a node in the graph; simulating a reservoir in place of an inlet pipe to each of the pre-defined sub-networks; receiving an array of permissible pressure head values for the simulated reservoir; and iteratively computing for the pipes, dynamic feature values associated with the pipes, until an optimum pressure head value from the received pressure head values causes at least one node at a highest elevation in the pre-defined sub-network to have pressure values within a pre-defined range of minimum and maximum pressure for the sub-networks, wherein the dynamic feature values are approximate flow and pressure values corresponding to the received pressure head values. The computing device further computes the dynamic feature values including flow, mid-point static pressure, mid-point total pressure, static pressure difference and total pressure difference associated with the pipes corresponding to the optimum pressure head value.

In an embodiment of the present disclosure, the one or more hardware processors are further configured to train a classifier based on historic GIS data and the computed dynamic feature values; and classify, for a corresponding time interval in future, the pipes as "burst" or "no burst" based on the computed dynamic feature values.

In an embodiment of the present disclosure, the one or more hardware processors are further configured to rank the pipes based on a computed probability of burst, wherein the probability of burst is based on one or more combinations of the dynamic feature values.

In an embodiment of the present disclosure, the classifier is one of Naive Bayes, Support Vector Machines, Logistic Regression and Restricted Boltzmann Machines.

In an embodiment of the present disclosure, the one or more hardware processors are further configured to compute demand at each node based on uniform distribution of demands along the pipes having lowest diameters; and obtain roughness coefficient values for each pipe based on material thereof.

It is to be understood that both the foregoing general description and the following detailed description are exemplary and explanatory only and are not restrictive of the embodiments of the present disclosure, as claimed.

BRIEF DESCRIPTION OF THE DRAWINGS

The embodiments herein will be better understood from the following detailed description with reference to the drawings, in which:

FIG. 12A and FIG. 12B illustrate performance curves in terms of percentage bursts detected versus percentage network length covered with and without dynamic features using Logistic Regression (LR) classifier for a one year period and averaged across the years 2005-2011;

FIG. 13 illustrates comparative performance curves in terms of percentage bursts detected versus percentage network length covered for static features using NB, RBM, LR and SVM classifiers; and FIG. 14 illustrates comparative performance curves in terms of percentage bursts detected versus percentage network length covered for dynamic features using NB, RBM, LR and SVM classifiers.

Figure 1:
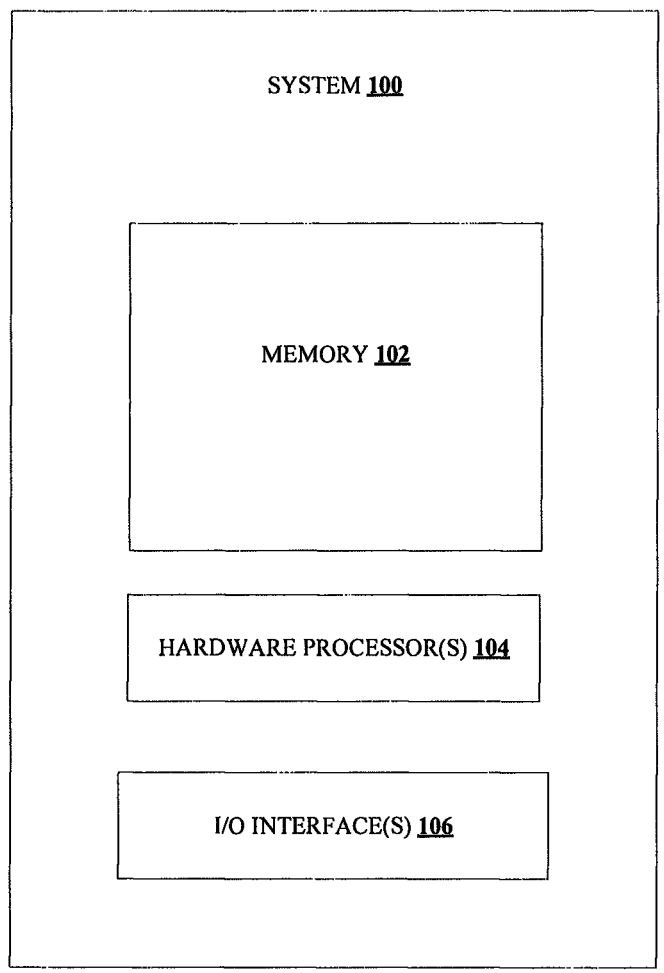
FIG. 1 illustrates an exemplary block diagram of a system for ranking pipes for maintenance in pipe networks using approximate hydraulic metrics, in accordance with an embodiment of the present disclosure.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Before setting forth the detailed explanation, it is noted that all of the discussion below, regardless of the particular implementation being described, is exemplary in nature, rather than limiting.

Bursting of pipes is a key issue that affects any pipe network. While some pipe networks such as oil and gas pipelines may be richly instrumented and sensed proactively in real-time to avert bursts, water pipelines have not received similar attention due to economic reasons and the nature of the damage caused. Conventional monitoring systems are plagued with issues pertaining to scalability, practicality or they depend on static features associated with specific pipes under consideration. The ideal option of providing a sensored network for monitoring may not be economical viable. Systems and methods of the present disclosure complement prior data-driven approaches by approximately estimating dynamic features of individual pipes and flow from readily available network structure and other data. The present disclosure proves that for the purpose of estimating burst likelihood, even approximate pressures and flows that preserve the relative ordering across pipes would be sufficient. Using an academic benchmark water network with a calibrated hydraulic model, the present disclosure shows that approximation preserves the ordering of pressure and flows across pipes and thus can help in ordering pipes by burst likelihood. In the context of the present disclosure, the expression "pressure" refers to pressure at the mid-point of a pipe.

Referring now to the drawings, and more particularly to FIGS. 1 through 14, where similar reference characters denote corresponding features consistently throughout the figures, there are shown preferred embodiments and these embodiments are described in the context of the following exemplary system and method.

FIG. 1 illustrates an exemplary block diagram of a system 100 for ranking pipes for maintenance in pipe networks using approximate hydraulic metrics, in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

Figure 2C:
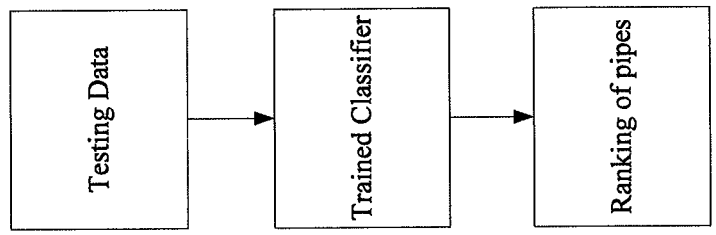
FIG. 2C is an exemplary flow chart illustrating high level steps involved in ranking of pipes under consideration, in accordance with an embodiment of the present disclosure.
Figure 2B:
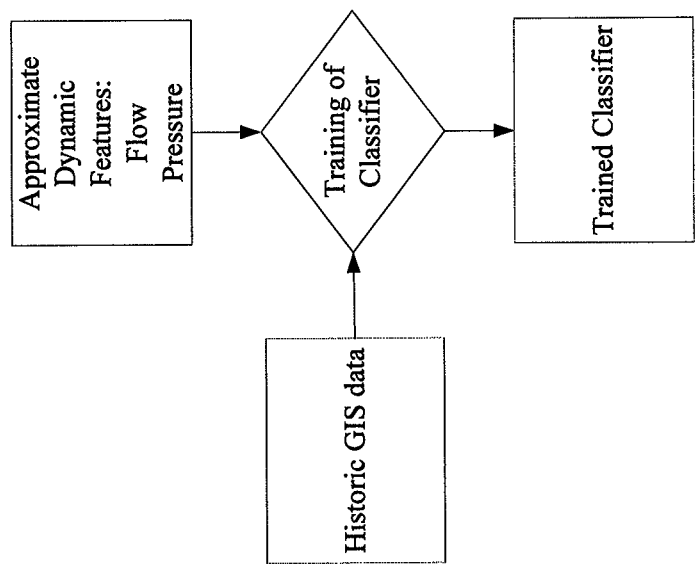
FIG. 2B is an exemplary flow chart illustrating high level steps involved in training of a classifier, in accordance with an embodiment of the present disclosure.
Figure 2A:
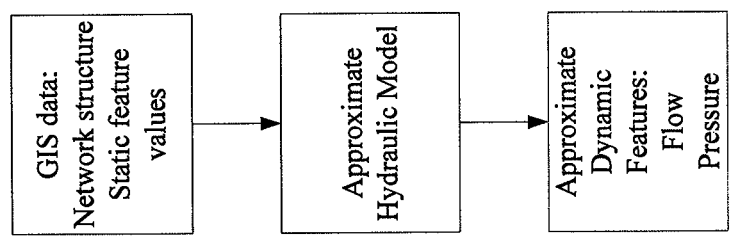
FIG. 2A is an exemplary flow chart illustrating high level steps involved in approximation of dynamic features, in accordance with an embodiment of the present disclosure.

FIG. 2A, FIG. 2B and FIG. 2C generally referenced by numeral 200 illustrate high level steps of the method of the present disclosure. Particularly, FIG. 2A is an exemplary flow chart illustrating high level steps involved in approximation of dynamic features, in accordance with an embodiment of the present disclosure; FIG. 2B is an exemplary flow chart illustrating high level steps involved in training of a classifier, in accordance with an embodiment of the present disclosure; and FIG. 2C is an exemplary flow chart illustrating high level steps involved in ranking of pipes under consideration, in accordance with an embodiment of the present disclosure.

Figure 3:
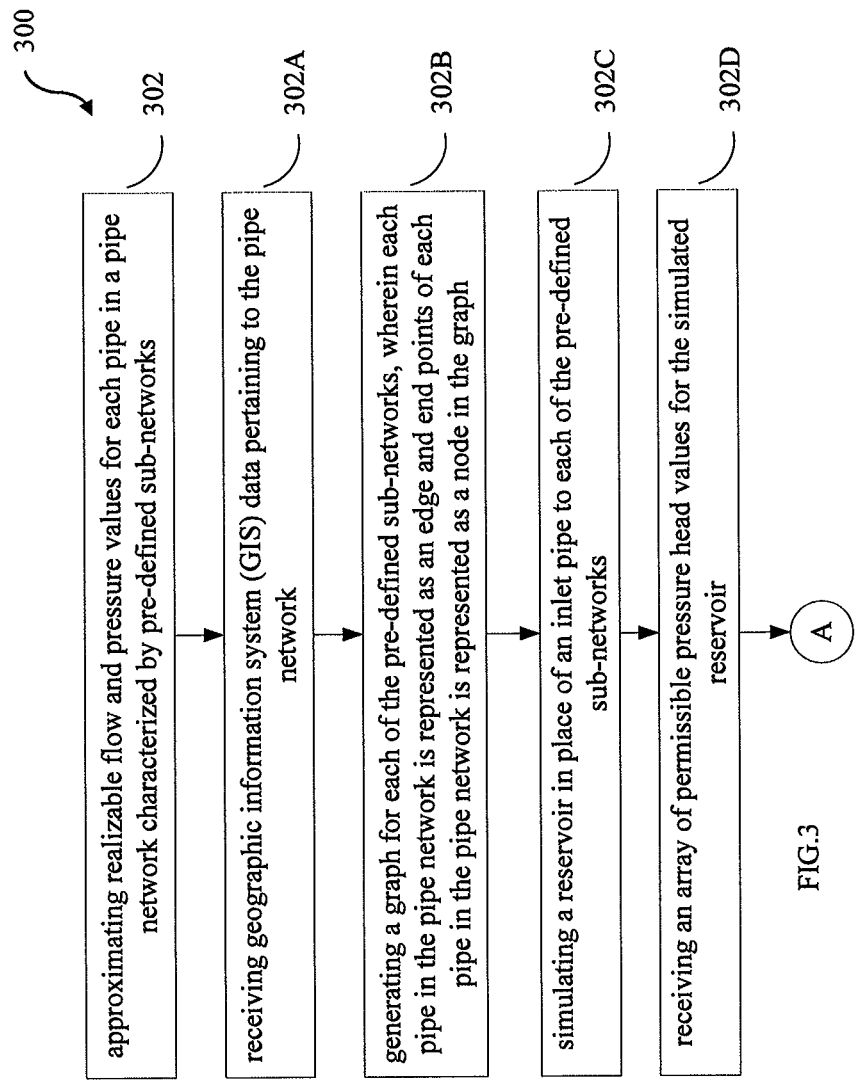
FIG. 3 is an exemplary flow diagram illustrating a computer implemented method for ranking pipes for maintenance in pipe networks using approximate hydraulic metrics, in accordance with an embodiment of the present disclosure.

FIG. 3 illustrates an exemplary flow diagram illustrating a computer implemented method 300 for ranking pipes for maintenance in pipe networks using approximate hydraulic metrics, in accordance with an embodiment of the present disclosure. In an embodiment, the system 100 comprises one or more data storage devices or memory 102 operatively coupled to the one or more processors 104 and is configured to store instructions configured for execution of steps of the method 300 by the one or more processors 104. FIG. 2A, FIG. 2B and FIG. 2C will now be explained in detail with reference to FIG. 3.

Although the systems and methods of the present disclosure may be explained herein below particularly with reference to water pipe networks, it may be noted that the present disclosure may be applicable to pipe networks carrying fluids such as gas, oil, and the like. Dynamic features of individual pipes such as pressure and flow arise due to the interplay between the network structure and the involved operations. Because pressure and flow of individual pipes arise from network-wide supply and demand constraints, they need to be either measured directly or computationally derived by solving a calibrated hydraulic model that simulates the operation of the network. Pressure and flow data is available only at the inlets of District Metering Areas (DMA's) (i.e., pre-defined sub-networks) of the utility or pipe networks. This is because pressure and flow sensors are typically deployed only at the DMA inlets. In many utilities the hydraulic model is typically not available for the entire network or is out of date due to the expensive calibration requirements. Systems and methods of the present disclosure address a technical problem of ranking pipes according to the probability of bursts in an impending year using dynamic features even in the absence of a calibrated hydraulic model wherein the only information available is historical burst data, basic pipe-level features, and the network structure.

Dynamic features such as pressure and flow depend on network-wide phenomena and can differentiate risk between pipes with identical static features and used differently in the network. In a typical utility network, treated water flows under pressure (due to higher elevation or pumping) from the sources through various pipes to the end-consumers. Each demand point on the network acts as a sink to the flows (and returns the flow to sewage network) and the demands at various points together influence the flows direction and magnitudes in the network. In addition, each pipe offers a resistance to the flow due to friction and thus pressure of the flow reduces as it passes through a pipe. The resistance would depend on the roughness coefficient, length, and diameter of the pipe.

Typically, the demand values at all nodes in the network, the reservoirs' capacities and pressures, the rating of all pumps in a water network, and the pipe characteristics including the roughness coefficients are assumed to be known inputs to a hydraulic model. The pressures at all nodes in the network and the flows through all pipes in the network are to be determined from these inputs.

TABLE 1

Notations used in the disclosure

| Symbol | Meaning |
|---|---|
| E | Pipes (edges, links) |
| V | Junctions (vertices, nodes) |
| $d_i$ | Demand at node i |
| $p_i$ | Static pressure at node i |
| $h_i$ | Elevation at node i |
| $\rho$ | Density of water (1 gm/cc) |
| g | Acceleration due to gravity 9.8 m/s$^2$ |
| $H_i$ | Total pressure at node i equals $p_i$ + $h_i \rho g$ |
| $C_{i,j}$ | Pressure gain due to pump along pipe (i, j) |
| $f_{i,j}$ | Flow from node i to node j |
| e | Edge (pipe) e = (i, j) |
| $L_e$ | Length of pipe e |
| $R_e$ | Radius of pipe e |
| $\mu_e$ | Roughness coefficient of pipe e |

Using the notation in Table 1, the equations that relate the desired outputs with the inputs can be stated as follows:
Flow Equation:

The flow entering a node i from all it neighbors $N_i$ is equal to the total flow leaving it plus the demand $d_i$ of the node i represented as $$\forall i \in V, d_i + \sum_{j \in N_i} f(i, j) = 0 \quad (1)$$

wherein, it is assumed that there are no leaks at junctions.
Pressure Equation:

For any link e=(i, j)∈E, the change in the total pressure H along the link may be represented as $$H_i + PumpingGain - Friction = H_j \quad (2)$$

With the total pressure $H_i$ re-written as the sum of the static pressure $p_i$ and the pressure due to elevation $h_i \rho g$, equation (2) may be expanded as $$p_i + h_i \rho g + C_{i,j} - \frac{L_e f_e^2 \times \rho g}{\mu_e R_e^5} = p_j + h_j \rho g \quad (3)$$

wherein equation (3) is a generalized version of Bernoulli's theorem that includes frictional losses.
These equations need to be solved using a form of fixed point iteration such as Todini's method, to obtain the pressure at all nodes; and flows through all pipes. The pressure and flows are the outputs of a hydraulic model.

From equations (1) and (3) it is observed that apart from the inputs (which includes $d_i$'s), the values of $\mu_e$'s should also be known to determine the pressures and flows. The $d_i$'s and $\mu_e$'s are empirically estimated for a utility water network during the process of hydraulic model calibration.

In most utility water networks, customers are not precisely metered at end-points and even if they are, the data is typically a monthly average. Demands are accurately measured only at aggregated levels. Therefore, node-level demands $d_i$'s may not be accurately known at the required spatio-temporal granularity. Further, as pipes age and corrode, the roughness of their internal surfaces changes, which affects the amount of pressure loss along the pipes. The roughness of a pipe, quantified by the roughness co-efficient ($\mu_e$), needs to be periodically estimated. These co-efficients can be estimated only when actual values of pressure and flows at various junctions and pipes are available. Finally, pump efficiencies affect the hydraulic model's accuracy. Aging pumps deviate significantly from manufacturer specifications. Considerable effort is required in terms of field trials and parameter fitting to estimate the $\mu_e$'s and pump efficiencies. For example, calibrating a network with few hundreds of nodes may take 40-60 days of effort by an expert team of 2-4 members. Larger networks require even more effort. A utility may not have in-house expertise to do such calibration, thus requiring expensive external consultants. For a network serving a population of 1 million, hydraulic model maintenance over a five year period typically costs about $4 million.

To obtain pressure and flow of various network pipes despite the unavailability of a calibrated hydraulic model, the method of the present disclosure proceeds as follows. As illustrated in FIG. 2A, firstly geographic information system (GIS) data is fed to an approximate hydraulic model to obtain approximate dynamic features. Accordingly, in an embodiment, at step 302, the one or more processors 104 of the system 100 are configured to approximate realizable flow and pressure values for each pipe in a pipe network characterized by pre-defined sub-networks (DMAs). The step of approximating includes receiving geographic information system (GIS) data pertaining to the pipe network at step 302A, wherein the GIS data may include static feature values associated with pipes in the pipe network such as one or more of diameter, length, age, connectivity, depth, past bursts data and material associated with the pipes.

The network structure obtained from the GIS system may be treated as a logical graph. The pipes that intersect in the GIS with common points are assumed to be vertices in the graphs; and pipes are the links. At step 302B, a graph is generated for each of the pre-defined sub-networks, wherein each pipe in the pipe network is represented as an edge and end points of each pipe in the pipe network is represented as a node in the graph. In accordance with the present disclosure, in place of an inlet pipe to each of the pre-defined sub-networks, a reservoir is simulated at step 302C.

In accordance with the present disclosure, a pseudo-hydraulic model is created based on following simplifying assumptions:

Demands are uniformly distributed along the pipes of the lowest diameters. Thus the average inflow into a DMA is divided across all demand points.

The roughness coefficients have not changed significantly from the initial values at the time of deployment.

Accordingly, in an embodiment, the step of simulating a reservoir in place of an inlet pipe further comprises computing demand at each node based on uniform distribution of demands along the pipes having lowest diameters; and obtaining roughness coefficient values for each pipe based on material thereof. Further an array of permissible pressure head values are received for the simulated reservoir at step 302D.

In an embodiment, at step 302E, dynamic feature values associated with the pipes are iteratively computed for all the pipes, until at least one node at a highest elevation in the pre-defined sub-network is computed to have pressure values within a pre-defined range of minimum and maximum pressure for the sub-networks. A corresponding pressure head value from the received pressure head values may be referred to as an optimum pressure head value. In an embodiment the dynamic feature values are approximate flow and pressure values corresponding to the received pressure head values. Once the approximate flow and pressure values are computed, the dynamic feature values such as flow, mid-point static pressure, mid-point total pressure, static pressure difference and total pressure difference associated with the pipes corresponding to the optimum pressure head value are computed at step 304.

In an embodiment, a pseudo code for computing the approximate dynamic features may be represented as

---

1. For a DMA in the network:
   edge e = pipe
   node i = end points of a pipe
   N = total number of nodes in the DMA
   F = Average inlet flow to the DMA
2. For every node i in the network:
   $d_i$ = demand at node i = F/N
   $h_i$ = elevation at node i
3. For every, edge e = (i, j) in the network:
   $L_e$ = Length of the pipe e
   $R_e$ = Radius of the pipe e
   $\mu_e$ = Roughness coefficient of the pipe e
4. $H_{r\_values}$ = Array of permissible head values for a reservoir in steps of 0.25m
   For example $H_{r\_values}$ = [200, 200.25, 200.50, ....220]
5. $H_r$ = Head at the reservoir (Inlet of the DMA)
   head_index = (0 + length($H_{r\_values}$)) /2
   Initialize $H_r$ = $H_{r\_values}$[head_index]
6. Using fixed point iteration solve for flow and pressure equation.
7. Obtain dynamic features:
   $P_i$ = Static pressure of node i
   $H_i$ = Total pressure of node i
   $f_{ij}$ = Flow from node i to node j
8. i_max_elev. = node with max h (elevation)
   if $P_{i\_max\_elev}$ < 40 Psi:
       head_index = head_index + 1
       set $H_r$ = $H_{r\_values}$[head_index]
       go to step 6
   else if $P_{i\_max\_elev}$ > 42 Psi:
       head_index = head_index − 1
       set $H_r$ = $H_{r\_values}$[head_index]
       go to step 6
   else:
       compute all the other dynamic features of the network:
       $P_{ij}$ = Static pressure at the mid-point of pipe with end nodes i and j
       = $(P_i + P_j)/2$
       $H_{ij}$ = Total pressure at the mid-point of pipe with end nodes i and j
       = $(H_i + H_j)/2$
       $sPD_{ij}$ = Static Pressure difference of pipe with end nodes i and j
       = $P_i − P_j$
       $tPD_{ij}$ = Total Pressure difference of pipe with end nodes i and j
       = $H_i − H_j$
9. Go to step 4 for other Reservoirs in the DMA
10. Go to step 1 for other DMAs in the network.

---

With the simplifying assumptions mentioned above, in accordance with the present disclosure, an approximate hydraulic model is solved using fixed point iteration and the pressures at nodes and flows through various pipes are obtained. It may be noted that if demands vary with time, time-averaged values of the pressures and flows through the pipe network may be evaluated.

As illustrated in FIG. 2B, a classifier is trained using the computed approximated dynamic features and historic GIS data to obtain a trained classifier. Accordingly, in accordance with the present disclosure, at step 306, a classifier is trained based on historic GIS data and the computed dynamic feature values. In an embodiment, the classifier is one of Naive Bayes, Support Vector Machines, Logistic Regression and Restricted Boltzmann Machines. Say historic GIS data is available for a previous year. For the impending year (time interval in future), the pipes may then be classified at step 308 as "burst" or "no burst" based on the computed dynamic feature values. As illustrated in FIG. 2C, the trained classifier receives testing data pertaining to the year for which pipe bursts need to be predicted and the pipes are ranked. Accordingly, in accordance with the present disclosure, at step 310, the pipes may be ranked based on a computed probability of burst, wherein the probability of burst is based on one or more combinations of the dynamic feature values. In an embodiment, higher the probability of burst associated with a pipe, higher may be the rank assigned to the pipe for scheduling maintenance.

Experimental Data

Using a real-world pipe burst dataset obtained from a European water utility for multiple years, the present disclosure shows that using approximate dynamic features computed by the system of the present disclosure, the ability of both generative and discriminative classifiers to predict pipe bursts is improved. The performance (as measured by the Area under the curve or the AUC score) of the best generative and discriminative classifiers improve by more than 25% through these features. Among the dynamic features considered, it was seen that pressure is more helpful in improving the burst prediction than flow.

The dataset from the European water utility pertains to pipes laid between the years 1930 to 2012. However, bursts were logged historically only from 2005. The network has around 6785 pipes with a total length of 415 kilometers. The network is divided into 16 DMA's (District Metering Areas) which are sub-networks over which flows can be controlled and monitored at few points of entry. For each DMA, the average flow entering the DMA (over a typical day) was known. The static data available for each pipe included length, diameter, depth of burial, material, and the approximate date of laying the pipe. Most of the pipes were laid in 1959-1964 (around 34% of the network). The ranges of the attributes are summarized in Table 2.

TABLE 2

Attributes available about network pipes - as obtained from the utility

| Attributes | Range | Unit |
| --- | --- | --- |
| Date laid | 1930-2011 | Years |
| Diameter | 13-600 | millimeters |
| Length | 0.5-1580 | meters |
| Depth | 0.6-1.5 | meters |
| Material | PVC, Cast Iron, Spun Iron, Poly-Ethylene and their variants. | |

Figure 5:
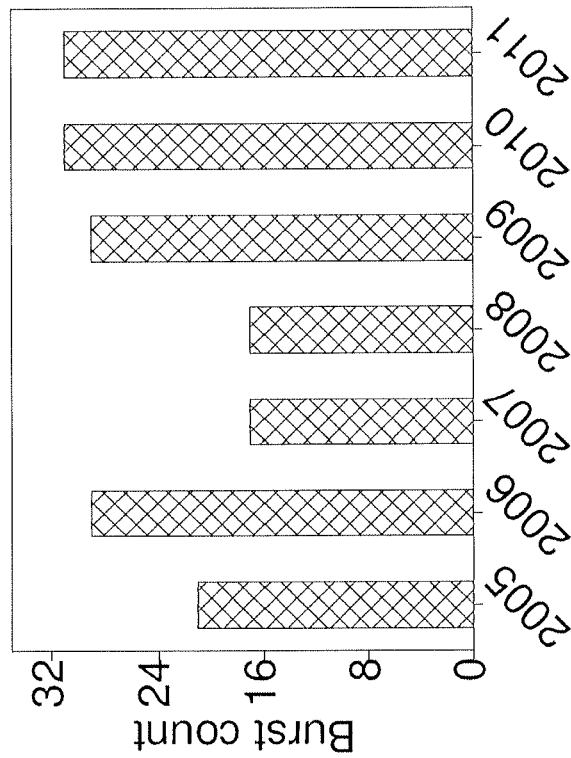
FIG. 5 illustrates historic data from a European water utility pertaining to burst count across years 2005-2011 in large diameter pipes of a pipe network.
Figure 4:
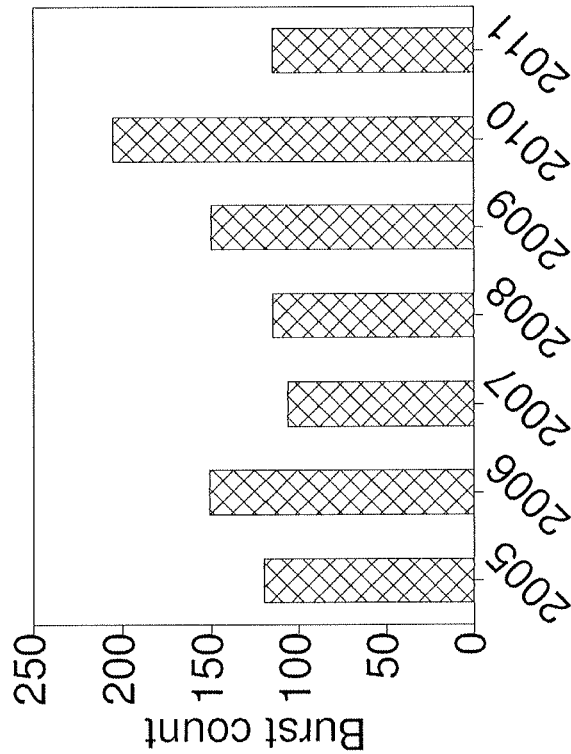
FIG. 4 illustrates historic data from a European water utility pertaining to burst count across years 2005-2011 in a pipe network.
Figure 6:
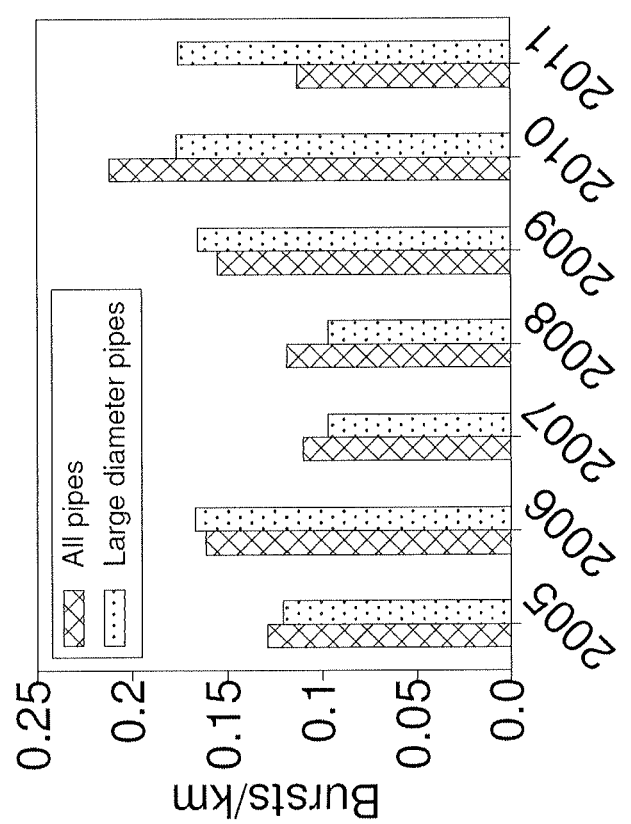
FIG. 6 illustrates historic data from a European water utility pertaining to burst/km of pipe length across years 2005-2011 in a pipe network.

The utility network structure was available using a GIS system that recorded the connectivity between the various pipes and identified the inlets to each of the DMA's. The bursts are logged by the utility when reported and repaired. There were around 962 bursts spread over 2005-2011. The break-up of the burst count across years is summarized in FIG. 4-6, wherein FIG. 4 illustrates historic data from the European water utility pertaining to burst count across years 2005-2011 in the pipe network; FIG. 5 illustrates historic data from the European water utility pertaining to burst count across years 2005-2011 in large diameter pipes of the pipe network; and FIG. 6 illustrates historic data from the European water utility pertaining to burst/km of pipe length across years 2005-2011 in the pipe network. The key observations from these graphs are that bursts are relatively rare events; and the burst rate of large diameter pipes is roughly the same as that of all pipes.

Bursts in large diameter pipe (i.e., diameter >125 mm) create more damage than a burst from a small diameter pipe. These pipes are also more expensive to fix. Accordingly, the present disclosure focuses on predicting bursts in large diameter pipes. In addition to the network connectivity and burst data from the utility, the elevation data for the entire network is obtained from Google™ maps at a spatial resolution of 150 meters. Elevation data is used since the terrain's elevation affects the water flow/pressure in the pipes.

The present disclosure firstly validates whether the computed approximate pressures and flows are close to expected values in reality, especially with respect to the relative ordering across pipes based on a fully calibrated benchmark water network available from the University of Exeter. The Wolf-Cordera (Colorado Springs) network has 1981 pipes serving an average demand of 3.7 million gallons per day. In this network, the flows and pressures are evaluated under two sources of error:

The demands are uniformly distributed across nodes, which is not the case in the calibrated model input. Assuming that demands are uniformly distributed results in an average relative error of approximately 42% across all the nodes.

The roughness coefficient is varied from the values given in the calibrated model. Specifically, the roughness coefficients of all the pipes are assumed to be that of a newly laid cast iron pipe.

Figure 7B:
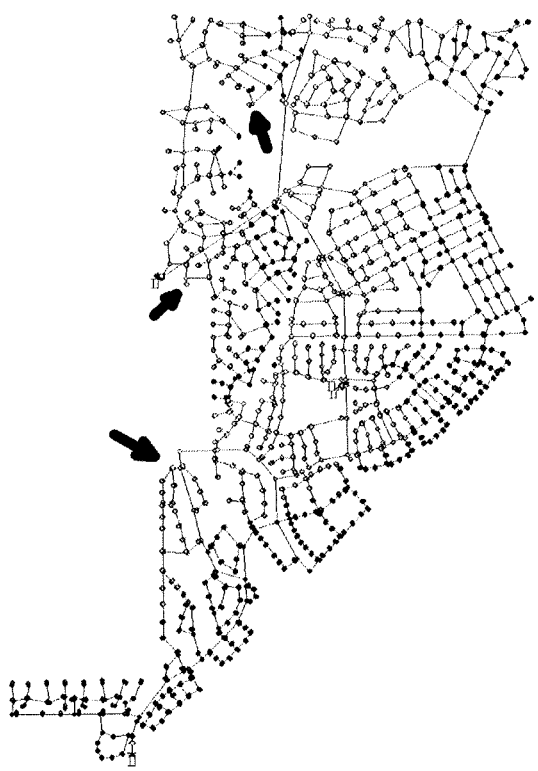
FIG. 7A and FIG. 7B illustrate color-coded relative ranking of pressures across network nodes as per the accurate hydraulic model and approximate hydraulic model of the present disclosure respectively.
Figure 7A:

FIG. 7A and FIG. 7B illustrate color-coded relative ranking of pressures across network nodes as per the accurate hydraulic model and approximate hydraulic model of the present disclosure respectively. Visually, the two distributions look very similar thereby indicating that the approximation has not changed the relative ordering. Similar color patterns across FIG. 7A and FIG. 7B indicate similar relative ordering of pressure; some changes are identified by arrows in the approximate hydraulic model of FIG. 7B. The present disclosure further illustrates quantification of the same. For each dynamic feature F, a set of top k pipes (ranked by F) were picked in both the approximate model with errors $\varepsilon_k$ of the present disclosure and actual calibrated model $A_k$. Then a measure of usefulness of approximation in identifying the top k pipes according to feature F is computed as $$\frac{\varepsilon_k \cap A_k}{k}$$

Figure 8:
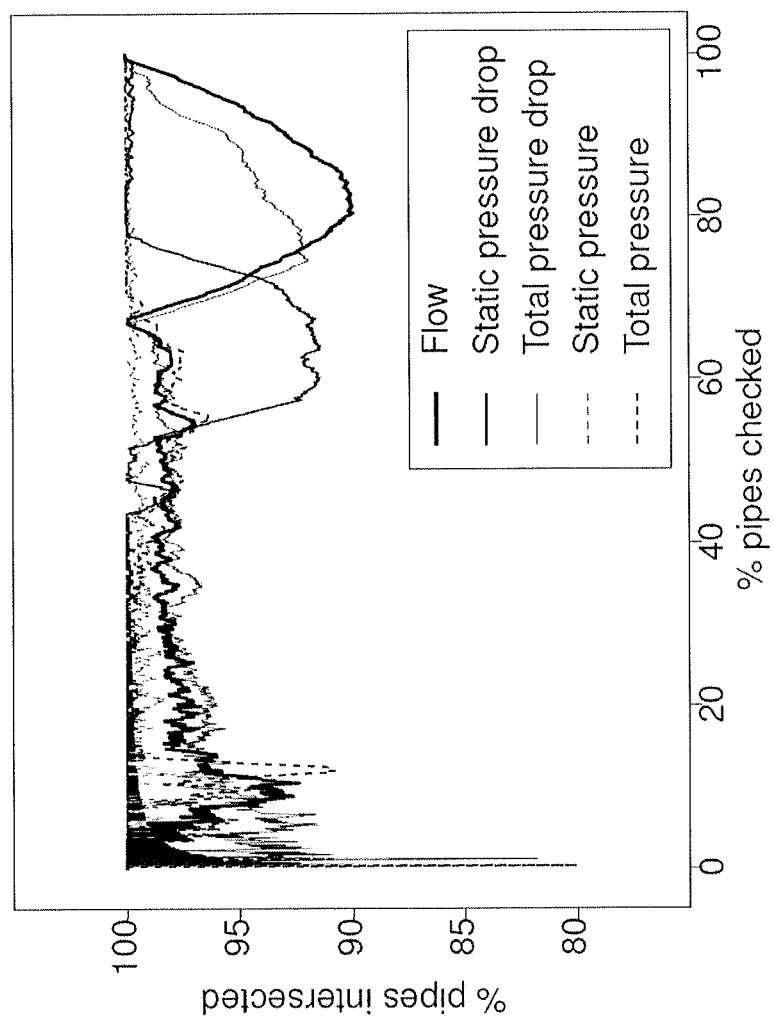
FIG. 8 illustrates percentage of pipes intersected versus percentage of pipes checked in accordance with the approximate hydraulic model of the present disclosure.

FIG. 8 illustrates the measure for various dynamic features in the form of percentage of pipes intersected versus percentage of pipes checked in accordance with the approximate hydraulic model of the present disclosure. Each curve shows the result for a specific feature. The dynamic features considered are: (a) flow through a pipe, (b) total pressure for a pipe (midpoint), (c) static pressure for a pipe (midpoint), (d) total pressure drop across a pipe, and (e) static pressure drop across a pipe. Apart from the initial few values of k, it is noted that the overlap between the sets identified by the approximate and actual models are close to around 95%. Even for high values of k, the minimum overlap between the sets is around 90%. The ordering is such that some pipes are initially omitted and then later added to the number of pipes being considered. So there is a dip and then the percentage comes back up. Summarizing, it is noted that despite the errors in estimating demands and the roughness coefficients the relative ordering across pipes is preserved according to the ranking for various dynamic features. It is noted that the simplifying approximations made in accordance with the present disclosure most certainly introduces errors in the actual values of the pressures and flows through pipes. However, since the relative ordering is preserved, it may be hypothesized that the errors in the actual values may not affect the classifiers much and therefore using even approximate dynamic feature values may assist in predicting bursts.

Using approximate dynamic features, the systems and methods of the present disclosure were then tested for predicting bursts in water networks. Actual burst data from a real world water utility are available from year 2005 to 2011 as mentioned above. The prediction model uses the available data/features of all the pipes that were laid until the end of current year and predict their ranks based on the break probabilities for the next year. Correspondingly, the training set for the model consisted of feature values of all pipes that were laid until the end of 2008 and their break/class information from 2009. The set of all features available for a classifier to predict pipe bursts are summarized in Table 3.

TABLE 3

| Features available for burst prediction | |
|---|---|
| | Value type |
| Static Features | |
| Length | Continuous |
| Diameter | Continuous |
| Age | Continuous |
| Connectivity | Continuous |
| Material | Categorical |
| Depth | Continuous |
| # of bursts occurred | Continuous |
| Dynamic features | |
| Total pressure | Continuous |
| Static pressure | Continuous |
| Total pressure drop | Continuous |
| Static pressure drop | Continuous |
| Flow | Continuous |

In the dataset under consideration, all $2^7-1$ static feature combinations were considered and the best performing combination for each classifier type was identified. Similarly with the additional dynamic features, the best combination (out of $2^{12}-1$ choices) for the static and dynamic features over the training set were identified.

The classifier predicts the class of each pipe (i.e., burst or no burst) with an output probability. The output of the classifier is used as the rank of the pipe that is classified. First a classifier is trained on past data and then evaluated on a future year; the goodness of the classification is evaluated using a modified AUC score of the false-negative vs. false-positive curve. Suppose k pipes of lengths $L_1 \ldots L_k$ are examined first according to the ranking given by a classifier. These set of k pipes would entail certain percentage of actual bursts in the impending year (which is available from the ground truth data). Combining these two results in a point on the performance curve. Specifically, the X-coordinate of the point is given by a fraction of the total network length examined as $$\frac{\sum_{i=1}^{i=k} L_i}{\sum_{i=1}^{i=N} L_i}$$

The Y-coordinate shows the percentage of bursts in the k examined pipes as validated from the ground truth. This process is repeated for various ranks, k=1 . . . N, and the performance curve is obtained. To summarize, the X-axis in each of the figures is the % of the length of the network examined. The Y-axis shows the percentage of predicted bursts that are actually bursts (i.e. true positive rate).

To study the usefulness of the approximate dynamic features in predicting future pipe bursts, four different classifiers were tested, wherein two were discriminative and two were generative classifiers.

Naive Bayes Classifier:

The Naive Bayes classifier is a simple probabilistic model that evaluates the posteriori probability of a burst event B given the data feature vector x. Because the method assumes that conditioned on the class, the features are independent, $$P(B \mid x) = P(B) \prod_i P(x_i \mid B)$$

Figures 9A, 9B:
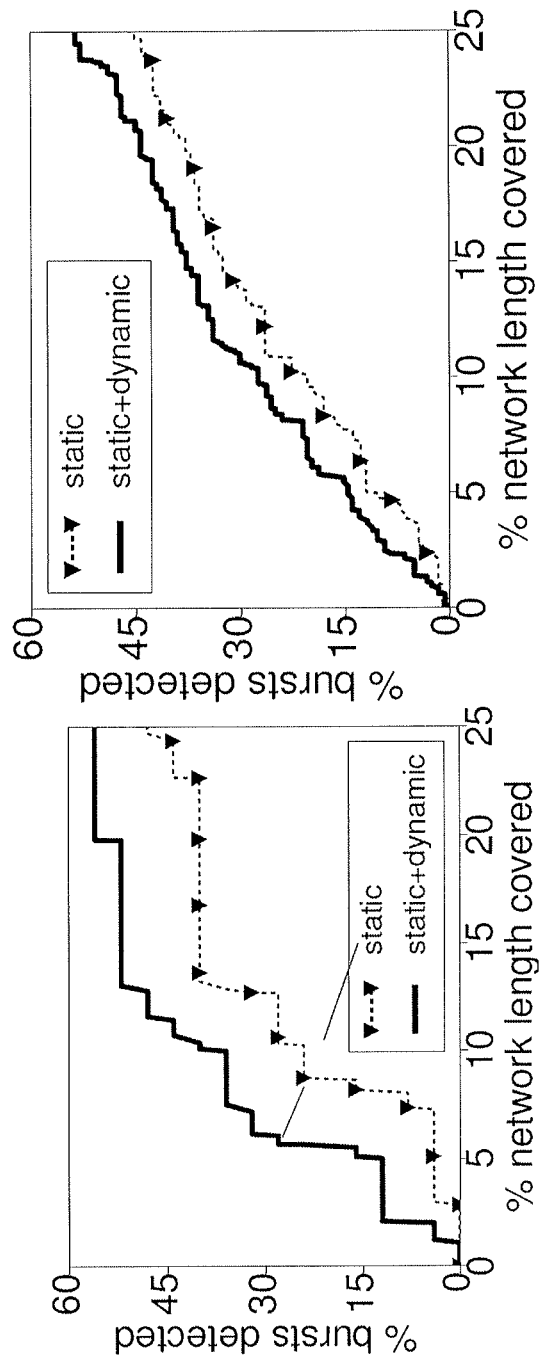
FIG. 9A and FIG. 9B illustrate performance curves in terms of percentage bursts detected versus percentage network length covered with and without dynamic features using Naive Bayes (NB) classifier for a one year period and averaged across the years 2005-2011.

The material of pipes is discrete and hence they are treated to be a multinomial feature; while the others are continuous and can be treated as Gaussian. Thus a Naive Bayes approach that mixes both Gaussian and multinomial distributions is used. In accordance with the present disclosure, the posteriori probabilities of the Gaussians and the multinomial distributions are evaluated separately and then combined. The pipes are ranked based on the posteriori probability of a burst for the pipes. FIG. 9A and FIG. 9B illustrate performance curves in terms of percentage bursts detected versus percentage network length covered with and without dynamic features using Naive Bayes (NB) classifier for a one year period and averaged across the years 2005-2011. Table 4 shows the average improvements (i.e., average of the improvements across all years) for varying budgets of examination.

TABLE 4

Naive Bayes-Average improvement for various pipe lengths examined. Note that the average is calculated across the improvements of 6 years.

| | % pipe length examined | | | | | |
|---|---|---|---|---|---|---|
| | 2 | 5 | 10 | 15 | 20 | 25 |
| % increase in prediction accuracy | 176.9 | 140.2 | 74.2 | 43.2 | 29.8 | 25.9 |

It is noted that there is a sharp jump in the improvement when moving to around 2% of the network length; which quickly falls off with increasing budgets. Thus the systems and methods of the present disclosure is especially useful for water utilities which have a significant budget constraint for proactively monitoring/maintaining the pipes.

Figures 10A, 10B:
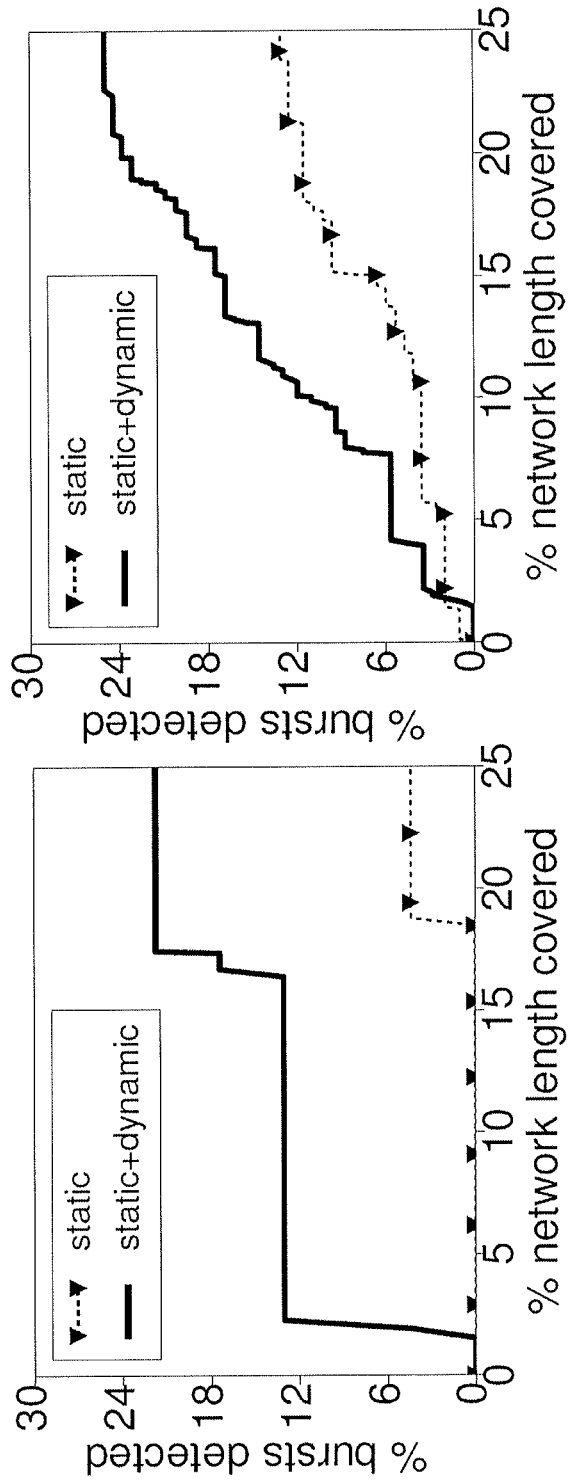
FIG. 10A and FIG. 10B illustrate performance curves in terms of percentage bursts detected versus percentage network length covered with and without dynamic features using Restricted Boltzmann Machine (RBM) classifier for a one year period and averaged across the years 2005-2011.

The best dynamic feature combination that does consistently better includes diameter, depth, connectivity, material, static pressure drop and static pressure in a pipe. In the best performing year, when 25% of the pipe length is examined, dynamic feature combinations detect 12 break pipes, while the best static feature combination picks 10 break pipes. Out of the 12 break pipes detected, 7 pipes have static pressure drop values that lie in the upper tail of the feature distribution (greater than 70th percentile value). Though there are some common break pipes that are detected by both dynamic and static feature combination, the ranks of those pipes are moved significantly to the top order when dynamic features are considered. This may help the utility when they are to examine a lesser percentage of the network pipe length Restricted Boltzmann Machine (RBM) Classifier:

The RBM is a generative model that learns the probability distribution of the inputs and outputs a feature vector for each input. The features are sigmoidal functions of the weighted inputs, where the weights are learned by the stochastic maximum likelihood (SML) method. The features so obtained from the RBM are in turn used to train a classifier for determining the final output. As in the case with Naive Bayes classifier, using dynamic features with RBM shows a better performance than just the static features for classification. FIG. 10A and FIG. 10B illustrate performance curves in terms of percentage bursts detected versus percentage network length covered with and without dynamic features using Restricted Boltzmann Machine (RBM) classifier for a one year period and averaged across the years 2005-2011. The average of the improvement obtained across various years is tabulated in Table 5.

TABLE 5

RBM-average improvement for various pipe lengths examined across 6 years.

| | % pipe length examined | | | | | |
|---|---|---|---|---|---|---|
| | 2 | 5 | 10 | 15 | 20 | 25 |
| % increase in prediction accuracy | 50 | 51.2 | 139.5 | 98 | 810 | 337.4 |

The best feature combination that does consistently better includes static pressure and flow in a pipe. It is noted that this combination does not include any static feature. In the best performing year, when 20 percentage of the pipe length is examined, the dynamic feature combination is able to detect 4 break pipes, while the static feature combination could pick only one break pipe. Out of the 4 break pipes detected, 2 pipes have flow values greater than 85th percentile value and one has flow value greater than 60th percentile value. That is, they lie in the upper tail of the feature distribution.

Figures 11A, 11B:
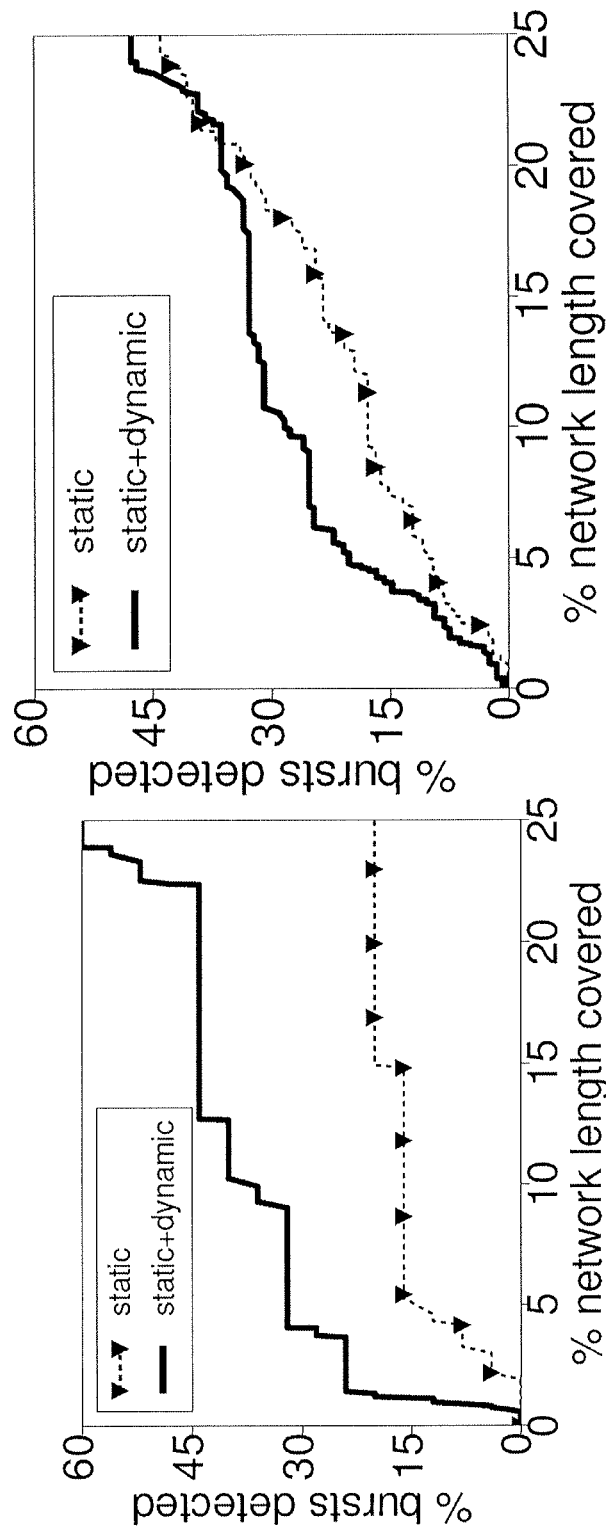
FIG. 11A and FIG. 11B illustrate performance curves in terms of percentage bursts detected versus percentage network length covered with and without dynamic features using Support Vector Machine (SVM) classifier for a one year period and averaged across the years 2005-2011.

Support Vector Machine (SVM) Classifier:

SVMs are supervised learning models that belong to the class of maximum margin classifiers. The margin is defined as the perpendicular distance from the decision boundary to the closest points on either side. They try to find a decision boundary that has maximum distance to the closest points in the training set, called support vectors. The goal of maximum margin classification is to separate the two classes by a hyper plane such that the distance to the support vectors is maximized. The present disclosure uses Platt scaling to convert classification decisions from an SVM to class ranks. It is again seen that using dynamic features with SVM shows a better performance than just the static features for classification. FIG. 11A and FIG. 11B illustrate performance curves in terms of percentage bursts detected versus percentage network length covered with and without dynamic features using Support Vector Machine (SVM) classifier for a one year period and averaged across the years 2005-2011. Table 6 shows the improvement over the years.

TABLE 6

Average improvement for various pipe lengths examined across 6 years.

| | (% pipe length examined) | | | | |
|---|---|---|---|---|---|
| | 2 | 5 | 10 | 15 | 20 | 25 |
| % increase in prediction accuracy | 100 | 412.8 | 88.8 | 63.9 | 40.8 | 39.4 |

The best performing dynamic feature combination includes diameter, depth, connectivity, and total pressure drop. The apparent out-performance of SVM with dynamic features at certain points is due to the low base performance. Specifically, for one of the years, the performance of the static features at 5% pipe length examination limit was very poor leading to the high relative performance improvement of dynamic features. In the best performing year, on examining 25% of the network length the best combination that includes dynamic features detects 40% additional breaks compared to best combination containing only the static features. This boost in the performance is because of 6 additional pipes detected by the best feature combination that belong to the upper tail (top 30 percentile) of the dynamic features.

Logistic Regression (LR):

As with Naive Bayes, Logistic Regression learns P(B|x). LR assumes a parametric form for the distribution P(B|x), and then directly estimates the parameters from the training data. Specifically, the parametric model assumed by LR in the case where B is Boolean is:

$$P(B \mid x) = \frac{\exp(w_o + \sum_{i=1}^{i=n} w_i x_i)}{1 + \exp(w_o + \sum_{i=1}^{i=n} w_i x_i)}$$

The model is trained and the AUC of the performance curves is obtained as discussed with Naive Bayes. FIG. 12A and FIG. 12B illustrate performance curves in terms of percentage bursts detected versus percentage network length covered with and without dynamic features using Logistic Regression (LR) classifier for a one year period and averaged across the years 2005-2011. Table 7 shows the improvement over static features for various values of the length examined.

TABLE 7

LR-Average improvement for various pipe lengths examined across 6 years.

| | (% pipe length examined) | | | | |
|---|---|---|---|---|---|
| | 2 | 5 | 10 | 15 | 20 | 25 |
| % increase in prediction accuracy | 52.7 | 21.9 | 28.3 | 20.6 | 106.9 | −13.3 |

An improved behavior for prediction using logistic regression was seen for lower values of the length examined. However, when higher fraction of pipe lengths are examined, the performance actually degrades. This suggests that at higher fraction of pipe lengths LR is 'led astray' by the additional dynamic features. In other words, LR is not able to learn the information content in the dynamic features and combine it appropriately with those in the other static features. The best performing combination included the static feature depth; and the dynamic feature of flow, total pressure drop and total pressure.

It is noted that across all classifiers considered, the age, length, and the number of bursts are not chosen in the best combination of results. Because the methods choose pipes according to the probability normalized by the length, length is disfavored. Age and past history of bursts are expected to influence burst predictions. However, this behavior was not observed in the specific data-set tested. This behavior may be because the record-keeping of the age of pipes is not correct or because the age and history of bursts is already part of the standard risk matrix methodology and so bursts which can be caught by those may have already been avoided by the utility.

FIG. 13 illustrates comparative performance curves in terms of percentage bursts detected versus percentage network length covered for static features using NB, RBM, LR and SVM classifiers and FIG. 14 illustrates comparative performance curves in terms of percentage bursts detected versus percentage network length covered for dynamic features using NB, RBM, LR and SVM classifiers. In accordance with the systems and methods of the present disclosure, following inferences were noted:

Dynamic features help across three of the four classifiers studied suggesting that even approximate network operational information can help utilities improve their detection of bursts. The top two classifiers—Naive Bayes and SVM get a considerable performance boost by using the approximate dynamic features across the entire range of pipe lengths studied.

It is noted that the pressures seem to help the most and flows seem to help the least. This may be due to the methodology of estimating the feature values. The errors in the nodal demands could be more significant than those in the roughness coefficients in the approximate hydraulic model.

The order of relative performance of the classifiers changes with dynamic features suggesting that some classifiers are better able to learn the additional information available from the dynamic features.

The performance with RBM which was convex (below the 45 deg. line) has improved with the additional features to a pseudo-concave curve.

Across all classifiers, it was noted that pressure drop in a pipe is more correlated with bursts than the actual pressure in a pipe. Most of the best feature combinations include the pressure drop in a pipe.

The written description describes the subject matter herein to enable any person skilled in the art to make and use the embodiments of the present disclosure. The scope of the subject matter embodiments defined here may include other modifications that occur to those skilled in the art. Such other modifications are intended to be within the scope if they have similar elements that do not differ from the literal language of the claims or if they include equivalent elements with insubstantial differences from the literal language.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments of the present disclosure may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules comprising the system of the present disclosure and described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device. The various modules described herein may be implemented as software and/or hardware modules and may be stored in any type of non-transitory computer readable medium or other storage device. Some non-limiting examples of non-transitory computer-readable media include CDs, DVDs, BLU-RAY, flash memory, and hard disk drives.

Further, although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

It is intended that the disclosure and examples be considered as exemplary only, with a true scope and spirit of disclosed embodiments being indicated by the following claims.

What is claimed is:

1. A processor implemented method (300) comprising:
approximating realizable flow and pressure values for each pipe in a pipe network characterized by pre-defined sub-networks (302), the step of approximating comprising:
receiving geographic information system (GIS) data pertaining to the pipe network, the GIS data including static feature values associated with pipes in the pipe network, the static features comprising one or more of diameter, length, age, connectivity, depth, past bursts data and material associated with the pipes (302A), wherein the geographic information system (GIS) data is fed to an approximate hydraulic model to obtain approximate dynamic features;
generating a graph for each of the pre-defined sub-networks, wherein each pipe in the pipe network is represented as an edge and end points of each pipe in the pipe network is represented as a node in the graph (302B);
simulating a reservoir in place of an inlet pipe to each of the pre-defined sub-networks (302C);
receiving an array of permissible pressure head values for the simulated reservoir (302D); and
iteratively computing for the pipes, dynamic feature values associated with the pipes, until an optimum pressure head value from the received pressure head values causes at least one node at a highest elevation in the pre-defined sub-network to have pressure values within a pre-defined range of minimum and maximum pressure for the sub-networks, wherein the dynamic feature values are approximate flow and pressure values corresponding to the received pressure head values (302E); and computing the dynamic feature values including flow, mid-point static pressure, mid-point total pressure, static pressure difference and total pressure difference associated with the pipes corresponding to the optimum pressure head value (304).

2. The processor implemented method of claim 1 further comprising:

training a classifier based on historic GIS data and the computed dynamic feature values (306); and classifying, for a corresponding time interval in future, the pipes as "burst" or "no burst" based on the computed dynamic feature values (308).

3. The processor implemented method of claim 2 further comprising ranking the pipes based on a computed probability of burst, wherein the probability of burst is based on one or more combinations of the dynamic feature values (310).

4. The processor implemented method of claim 2, wherein the classifier is one of Naive Bayes, Support Vector Machines, Logistic Regression and Restricted Boltzmann Machines.

5. The processor implemented method of claim 1, wherein the step of simulating further comprises:

computing demand at each node based on uniform distribution of demands along the pipes having lowest diameters; and obtaining roughness coefficient values for each pipe based on material thereof.

6. A system (100) comprising:

one or more data storage devices (102) operatively coupled to one or more hardware processors (104) and configured to store instructions configured for execution by the one or more hardware processors to:

approximate realizable flow and pressure values for each pipe in a pipe network characterized by pre-defined sub-networks, the step of approximating comprising:

receiving geographic information system (GIS) data pertaining to the pipe network, the GIS data including static feature values associated with pipes in the pipe network, the static features comprising one or more of diameter, length, age, connectivity, depth, past bursts data and material associated with the pipes, wherein the geographic information system (GIS) data is fed to an approximate hydraulic model to obtain approximate dynamic features;

generating a graph for each of the pre-defined sub-networks, wherein each pipe in the pipe network is represented as an edge and end points of each pipe in the pipe network is represented as a node in the graph;

simulating a reservoir in place of an inlet pipe to each of the pre-defined sub-networks;

receiving an array of permissible pressure head values for the simulated reservoir; and iteratively computing for the pipes, dynamic feature values associated with the pipes, until an optimum pressure head value from the received pressure head values causes at least one node at a highest elevation in the pre-defined sub-network to have pressure values within a pre-defined range of minimum and maximum pressure for the sub-networks, wherein the dynamic feature values are approximate flow and pressure values corresponding to the received pressure head values; and computing the dynamic feature values including flow, mid-point static pressure, mid-point total pressure, static pressure difference and total pressure difference associated with the pipes corresponding to the optimum pressure head value.

7. The system of claim 6, wherein the one or more hardware processors are further configured to:

train a classifier based on historic GIS data and the computed dynamic feature values; and classify, for a corresponding time interval in future, the pipes as "burst" or "no burst" based on the computed dynamic feature values.

8. The system of claim 7, wherein the one or more hardware processors are further configured to rank the pipes based on a computed probability of burst, wherein the probability of burst is based on one or more combinations of the dynamic feature values.

9. The system of claim 7, wherein the classifier is one of Naive Bayes, Support Vector Machines, Logistic Regression and Restricted Boltzmann Machines.

10. The system of claim 6, wherein the one or more hardware processors are further configured to:

compute demand at each node based on uniform distribution of demands along the pipes having lowest diameters; and obtain roughness coefficient values for each pipe based on material thereof.

11. A computer program product comprising a non-transitory computer readable medium having a computer readable program embodied therein, wherein the computer readable program, when executed on a computing device, causes the computing device to:

approximate realizable flow and pressure values for each pipe in a pipe network characterized by pre-defined sub-networks, the step of approximating comprising:

receiving geographic information system (GIS) data pertaining to the pipe network, the GIS data including static feature values associated with pipes in the pipe network, the static features comprising one or more of diameter, length, age, connectivity, depth, past bursts data and material associated with the pipes, wherein the geographic information system (GIS) data is fed to an approximate hydraulic model to obtain approximate dynamic features;

generating a graph for each of the pre-defined sub-networks, wherein each pipe in the pipe network is represented as an edge and end points of each pipe in the pipe network is represented as a node in the graph;

simulating a reservoir in place of an inlet pipe to each of the pre-defined sub-networks;

receiving an array of permissible pressure head values for the simulated reservoir; and iteratively computing for the pipes, the dynamic feature values associated with the pipes, until an optimum pressure head value from the received pressure head values causes at least one node at a highest elevation in the pre-defined sub-network to have pressure values within a pre-defined range of minimum and maximum pressure for the sub-networks, wherein the dynamic feature values are approximate flow and pressure values corresponding to the received pressure head values; and compute the dynamic feature values including flow, mid-point static pressure, mid-point total pressure, static pressure difference and total pressure difference associated with the pipes corresponding to the optimum pressure head value.

12. The computer program product of claim 11, wherein the computer readable program further causes the computing device to:
   train a classifier based on historic GIS data and the computed dynamic feature values; and
   classify, for a corresponding time interval in future, the pipes as "burst" or "no burst" based on the computed dynamic feature values.

13. The computer program product of claim 12, wherein the computer readable program further causes the computing device to:
   rank the pipes based on a computed probability of burst, wherein the probability of burst is based on one or more combinations of the dynamic feature values.

* * * * *